United States Patent [19]

Lia

[11] Patent Number: 5,222,477
[45] Date of Patent: Jun. 29, 1993

[54] ENDOSCOPE OR BORESCOPE STEREO VIEWING SYSTEM

[75] Inventor: Raymond A. Lia, Auburn, N.Y.

[73] Assignee: Welch Allyn, Inc., Skaneateles Falls, N.Y.

[21] Appl. No.: 767,796

[22] Filed: Sep. 30, 1991

[51] Int. Cl.⁵ .............................................. A61B 1/06
[52] U.S. Cl. .......................................... 128/6; 128/4; 358/98
[58] Field of Search .................. 128/6, 4; 358/98, 88, 358/91, 92, 3

[56] References Cited

U.S. PATENT DOCUMENTS

| | | | |
|---|---|---|---|
| 4,134,644 | 1/1979 | Marks et al. | 358/88 X |
| 4,305,095 | 12/1981 | Dallas | 358/3 X |
| 4,651,201 | 3/1987 | Schoolman | 358/98 |
| 4,734,756 | 3/1988 | Butterfield et al. | 358/88 X |
| 4,827,909 | 5/1989 | Kato et al. | 128/6 |
| 4,862,873 | 9/1989 | Yajima et al. | 128/6 |
| 4,924,853 | 5/1990 | Jones, Jr. et al. | 358/98 X |
| 4,926,257 | 5/1990 | Miyazaki | 358/98 |
| 4,945,408 | 7/1990 | Medina | 358/88 |
| 5,113,253 | 5/1992 | Pritchard et al. | 358/92 X |

Primary Examiner—Richard J. Apley
Assistant Examiner—Karen Ann Jalbert
Attorney, Agent, or Firm—Wall and Roehrig

[57] ABSTRACT

A stereo imaging and viewing system for a borescope or endoscope employs a miniature camera assembly in which are disposed a CCD imager or equivalent imager, a wide-angle focusing lens assembly with an effective aperture on the order of about f/2 or wider, and an aperture plate interposed in the optical path of the camera and adjacent the lens assembly. The aperture plate has left and right pupils therein situated on opposite sides of the optic axis of the lens assembly. The pupils are separated from one another by a predetermined pupil distance that is somewhat smaller than the lens diameter. The left image passes through the left pupil and is focused through a corresponding portion of the lens assembly onto the image plane of the imager and a right image passes through the right pupil and is focused by a corresponding portion of the lens assembly onto the image plane of the imager. A selective mechanism, such as alternate shutters or distinct color filters, separate the left and right views of the target sequentially. Left and right views are then presented to a display device for viewing the left and right views stereoscopically.

7 Claims, 1 Drawing Sheet

ENDOSCOPE OR BORESCOPE STEREO VIEWING SYSTEM

BACKGROUND OF THE INVENTION

This invention relates to borescopes or endoscopes of the type in which a miniature video camera is mounted at a distal viewing head of an elongated insertion tube. The invention is more particularly concerned with an arrangement of the miniature video camera which produces left-eye and right-eye stereo images using a single video imaging device and a single lens assembly.

Recently, interest has increased in the use of video instruments for surgical applications to permit a surgeon to carry out a procedure with minimal intervention in the patient. An example of one such video instrument is a laparoscope for performing surgery in the abdominal cavity, where the instrument is inserted through a small incision. Unfortunately, a video laparoscope or other optical laparoscope provides only a two-dimensional view of the area where surgery is to be performed. Consequently, there is an interest in stereo laparoscopy to aid the surgeon in identifying and repairing or removing tissues in question. There is also an increased interest in remote imaging of industrial process, such an inspection of heat exchanger tubes or of turbine engines, where stereoscopic imaging could be employed to advantage.

However, in all previous stereoscopic systems, two stereoscopic images are generated from two separate optical systems. The images are then displayed separately to the left and right eyes of the surgeon or other observer, giving the perception of three dimensional imaging. The two separate images must be created with the same magnification, orientation, focus, and optical qualities. This presents a significant manufacturing problem due to tolerance, repeatability and assembly. The cost of such an instrument would be more than double the cost of a standard, two dimensional video imager, because two sets of optical lens assemblies, two cameras, and two electronic imagers, must be employed, and these must be matched and aligned to the maximum extent possible to display an acceptable stereoscopic pair of images on a video monitor. Moreover, because two separate camera systems are required, a three-dimensional imaging laparoscope or other endoscope or borescope would be significantly bulkier and heavier than a corresponding two-dimensional imaging instrument.

At the time being, full-color video borescopes and endoscopes are well known, and have been described, for example, in Danna et al. U.S. Pat. No. 4,491,365, Danna et al. U.S. Pat. No. 4,539,586, and Longacre et al. U.S. Pat. No. 4,523,224. The latter describes a color-sequential system in which sequential primary color light is supplied over a fiber optic bundle to illuminate a target area sequentially with primary color light.

OBJECT AND SUMMARY OF THE INVENTION

Accordingly, it is an object of this invention to provide a simple and efficient stereo imaging camera system for a borescope or endoscope.

It is another object of this invention to provide a stereoscopic imaging and viewing system for a borescope or endoscope in which a single optical lens system and a single CCD or other imaging system, which could include a fiber-optic bundle or a relay lens system, provides both right and left eye images from right and left perspectives.

In accordance with one aspect of this invention, a miniature camera assembly, which is disposed at the distal tip of a probe, such as a borescope or endoscope insertion tube, includes a CCD imager or the like, a wide-angle focusing lens assembly having a wide effective aperture, i.e. on the order of f/2 or greater, for focusing on the image plane of the imager an image of a three dimensional target in the viewing field of the camera assembly, and an aperture plate that is interposed in the optical path of the camera assembly adjacent the lens assembly. The aperture plate is provided with left and right pupils or apertures. These pupils are situated on opposite sides of the optic axis of the lens assembly. The two pupils are separated from one another by a predetermined pupil distance that is less than the lens assembly effective diameter, such that a left image passes through the left pupil and is focused by a corresponding portion of the lens assembly onto the image plane, while the right image passes through the right pupil, and is focused by a corresponding portion of the lens assembly onto the image plane. An image selecting device, such as a pair of alternately opening shutters, permit the left image and the right image to be formed alternately to provide alternate left and right eye views of the target. Alternatively, color filters could be employed at the respective left and right pupils, so that an image of one wavelength would be created through the left pupil and an image of a different wavelength would be produced through the right pupil. As a further alternative, if the imager includes a fiberoptic bundle rather than a solid state or CCD imager, the stereo viewing system could incorporate shutters or color filters over the respective pupils or apertures, and the surgeon could view the image displayed on a monitor through matching shutters or color filter glasses.

With this system, the optical focus and convergence points will be the same. That is, by adjusting the focus, the convergence of the two images is achieved, i.e., left and right images are brought into proper adjustment or registry. With the system of this invention, manufacturing is made as simple and cost effective as a standard optical assembly because only a single lens assembly and single imager are employed.

The above and many other objects, features, and advantages will become more fully appreciated from the ensuing description of the preferred embodiment which should be read in connection with the accompanying Drawing.

DETAILED DESCRIPTION OF THE PREFERRED EMBODIMENTS

Figure 1:
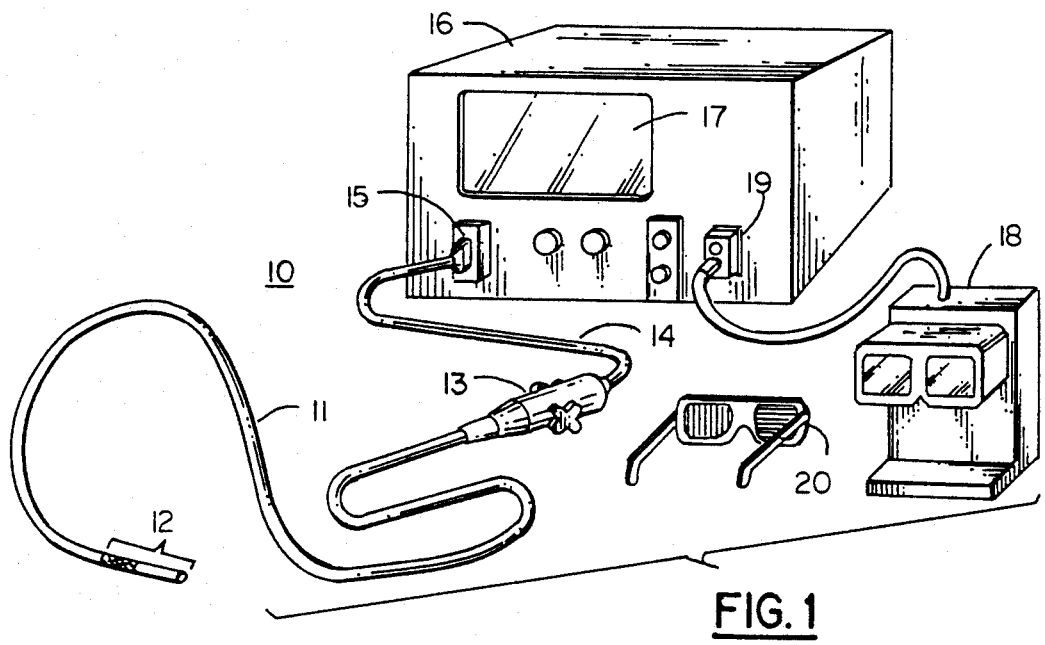
FIG. 1 is a perspective view of an endoscope or borescope according to one embodiment of this invention.

With reference to the Drawing, FIG. 1 shows a video borescope or endoscope assembly 10, in this case having an elongated, flexible insertion tube 11 with a viewing head 12 situated at its distal tip. In other embodiments, the probe could be a hard rigid tube. The viewing head contains optical lenses and a miniature camera to be described below. At the proximal end of the insertion tube 11 is a steering and control unit 13 which couples the insertion tube to a flexible tubular or umbilical extension 14. At the proximal end of the umbilical 14 is an interface module or connector 15 of the plug-in type, for example, as disclosed in U.S. Pat. No. 4,539,586. The connector module 15 fits a mating receptacle in a video processor 16. Included in the processor 16 is a video monitor screen 17, which can be, e.g. a color CRT monitor, a liquid crystal display, or other suitable display device. In this instance, a stereoscopic viewer 18, of the type having separate images for viewing with the left eye and right eye, is coupled to the processor 16 with a plug-in connector 19 fitting into a corresponding socket or receptacle on the processor 16. Stereoscopic viewing glasses 20 can also be provided which alternately shutter similarly to the apertures in the optical lens cell or have one red lens and one blue lens for color separation stereo techniques. In one viewing mode, the left-eye view and the right-eye view of the target can be presented on the screen 17 in general registry, so that the surgeon or other observer, wearing the glasses 20, will see the images presented in three-dimensional effect.

As mentioned above, within the distal tip 12 of the endoscope or borescope insertion tube there is a miniature camera 21, as described here and as shown, e.g., in FIGS. 2–5. In this embodiment, the camera 21 contains a CCD imager 22 which has an image plane 23 on which there are an array of pixels. In this embodiment, the imager 22 is a monochrome device, but in other embodiments, color filters can be provided so that the image outputs a standard RGB color video signal. A conductor bundle 24 or wiring harness carries the video signal back through the insertion tube 11 to the video processor 16.

As mentioned above, rather than a solid state electronic device, the imager 22 can take the form of a coherent fiber optic bundle wherein the image is conveyed over a multitude of optical fibers back to a not-shown camera or viewing device. Devices of this type are often referred to as fiberscopes.

Also in the miniature camera 21 is a focusing lens assembly 25 which acquires the image of a target in the viewing field of the camera and focuses the image onto the image plane 23. In this case, a wide-angle, lens assembly is employed, having an effective aperture of f/2 or wider. A transparent face plate 26 is disposed at the distal end of the camera 21 and includes means to seal the camera from environmental fluids.

Stereoscopic imaging is achieved with an aperture plate 27 which is interposed in the optical path of the camera adjacent the lens assembly 25. Depending on the nature of the lens elements employed, the aperture plate can be disposed between the lens elements as shown here, or in advance thereof or behind the lens elements. The aperture plate has formed therein a left pupil or aperture 28 and a right pupil or aperture 29, shown, e.g. in FIGS. 3 and 5. A shutter assembly 30 is disposed adjacent the aperture plate, and here has two shutters which open alternately. The shutter assembly is synchronized and controlled from the video processor 16, such that the right aperture 29 (FIGS. 2 and 3) and the left aperture 28 (FIGS. 4 and 5) are opened alternately to provide right-eye and left-eye views of the target, and these form left and right images that are each formed on the image plane 23 of the imager 22. In a preferred mode, liquid crystal shutters are employed as the shutter assembly 30, although mechanical shutters or other known systems could be used. For direct stereoscopic viewing, the left image (FIGS. 4 and 5) and the right image (FIGS. 2 and 3) can be separated in the video processor and then presented to separate viewing screens of the stereoscopic viewer 18. Alternatively, the left and right images can be presented simultaneously on the screen 17, which can then be viewed through the shuttering or colored glasses 20 or through other suitable viewing means, such as polarized glasses, etc.

Figures 2, 4, 6:
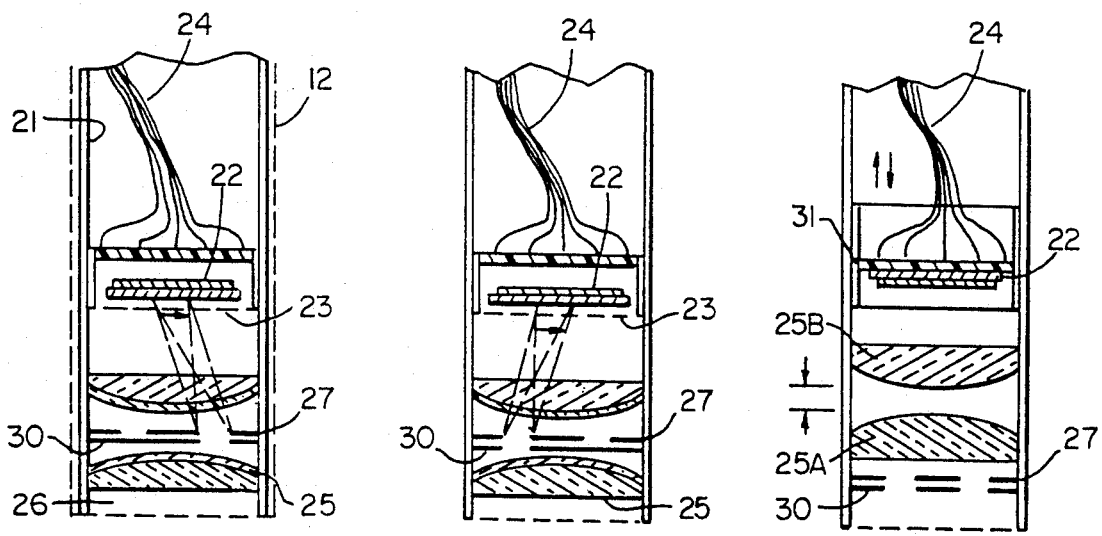
FIGS. 2 and 3 are a top section and a front view of a camera assembly, illustrating one embodiment and showing formation of an image through one pupil or aperture.
FIGS. 4 and 5 are a top section and a front view of a camera assembly showing formation of an image through the other pupil.
FIG. 6 is a top section illustrating another embodiment of this invention.

Another embodiment of the camera 21 is shown in FIG. 6, in which similar elements are identified with the same reference numbers as used previously. In this embodiment, a focusing sleeve 31 slides proximally-distally in the camera 21. The imager 22 is mounted in the sleeve 31 with the lenses 25 and aperture plate 27 and shutter assembly 30. The position of the focusing sleeve 31 is adjustable to focus the right and left images, and at the same time to converge the two images. In this case, the aperture plate 27 is disposed ahead of the lens element 25b, rather than between the lens elements 25a and 25b.

Figures 3, 5, 7:
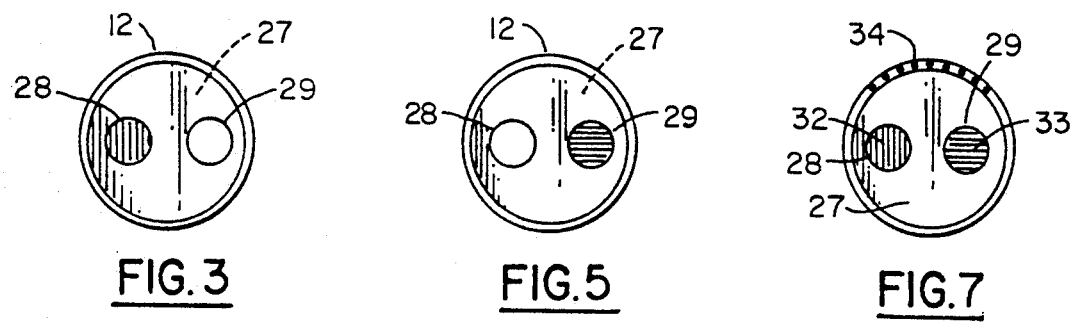
FIG. 7 is a front view illustrating a further embodiment of the invention.

As mentioned previously, rather than shutters, color filters can be employed with the respective apertures or pupils 28, 29 of the aperture plate 27, as shown in FIG. 7. Here, for example, a red filter 32 is employed with the left pupil 28 and a blue filter 33 is employed with the right pupil 29. In addition, a fiber optic bundle 34, which brings sequential color illumination from the video processor 16, has its distal end fanned out in an arc at the distal end of the camera assembly 21. The fiber optic bundle 34 provides red and blue light alternately, for example, from a color light wheel device of the type described in Longacre U.S. Pat. No. 4,523,224. The blue and red images are viewed only through the pupils 29 and 28, respectively and thus provide two sequential images which can be separated into right and left stereo images and viewed with suitable apparatus of the type described earlier. Alternatively, the two different color images can be viewed directly through the colored-lens glasses 20, if the image is carried over a fiberscope, as also described earlier.

While this invention has been described in detail with respect to certain preferred embodiments, it should be understood that the invention is not limited to those precise embodiments. Rather, many modifications and variations would present themselves to those skilled in the art without departing from the scope and spirit of this invention, as defined in the appended claims.

What is claimed is:

1. Stereoscopic imaging and viewing system for borescope or endoscope, comprising a miniature camera assembly that includes an imager having an image plane, a focusing lens assembly of a predetermined diameter and an effective aperture on the order of about f/2 or wider for focusing, at a location on an optic axis of the lens assembly, and on the image plane of said imager an image of a three-dimensional target in the viewing field of said camera assembly said imager being fixed against transverse movement with respect to said optic axis; an aperture plate interposed in the optical path of said camera assembly adjacent said lens assembly, having left and right pupils therein situated on opposite sides of the optic axis of said lens assembly and separated from one another by a predetermined pupil distance less than said lens assembly diameter, such that a left image passes through the left pupil and is focussed on the imager by a corresponding portion of said lens assembly on said image plane and a right image passes through the right pupil and is focussed on the imager by a corresponding portion of said lens assembly on said image plane; and selective means for alternately admitting light through said pupils and forming said left image and said right image on said imager alternately to produce distinguishable left-eye and right-eye views of the target; and viewing means coupled to said imager to receive the left and right images therefrom and visually display said left-eye and right-eye views of the target to produce a stereoscopic view of said three-dimensional target.

2. Stereoscopic imaging and viewing system of claim 1, wherein said imager and said lens assembly are controllably movable towards and away from each other with said aperture plate remaining with the lens assembly, such that relative movement of the focusing lens and imager plane of the imager simultaneously converges the left and right images.

3. Stereoscopic imaging and viewing system of claim 1 wherein said selective means includes a pair of shutter mechanisms which open alternately to produce the left and right images sequentially.

4. Stereoscopic imaging and viewing system of claim 3 wherein said shutter mechanisms include liquid crystal shutters.

5. Stereoscopic imaging and viewing system of claim 1 wherein said selective means includes left and right optical filters of distinct wavelengths disposed in the optical path of the associated left and right pupils.

6. Stereoscopic imaging and viewing system of claim 1 wherein said viewing means includes a video screen producing said right and left images in distinct colors thereon, and also comprises viewing glasses having left and right lenses of said distinct colors.

7. Stereoscopic imaging and viewing system of claim 1 wherein said viewing means comprises video processing means that includes a stereoscopic viewer with separate left and right images on which said left-eye and right-eye views are respectively presented.

* * * * *